United States Patent
Foltz et al.

(10) Patent No.: US 8,621,935 B2
(45) Date of Patent: Jan. 7, 2014

(54) METHOD AND APPARATUS FOR TESTING ATTACHMENT JOINTS

(75) Inventors: Gregory A. Foltz, Seattle, WA (US); Kirk B. Kajita, New Castle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/620,825

(22) Filed: Sep. 15, 2012

(65) Prior Publication Data
US 2013/0008259 A1  Jan. 10, 2013

Related U.S. Application Data

(62) Division of application No. 12/176,368, filed on Jul. 19, 2008, now Pat. No. 8,286,499.

(51) Int. Cl.
*G01N 3/24* (2006.01)

(52) U.S. Cl.
USPC .......................................................... 73/841

(58) Field of Classification Search
USPC .......................................................... 73/841
See application file for complete search history.

(56) References Cited

U.S. PATENT DOCUMENTS

| | | | |
|---|---|---|---|
| 4,084,029 A * | 4/1978 | Johnson et al. ............... | 428/119 |
| 4,597,278 A | 7/1986 | Hamada et al. | |
| 4,769,968 A | 9/1988 | Davis et al. | |
| 4,871,908 A | 10/1989 | Skuratovsky et al. | |
| 4,926,694 A | 5/1990 | Crews, Jr. et al. | |
| 4,958,522 A | 9/1990 | McKinlay | |
| 4,991,999 A | 2/1991 | Helms | |
| 5,048,347 A | 9/1991 | Knowles | |
| 5,511,432 A | 4/1996 | Holmes | |
| 5,619,837 A | 4/1997 | DiSanto | |
| 5,848,765 A * | 12/1998 | Gillespie ....................... | 244/124 |
| 6,415,577 B1 * | 7/2002 | Curtis ............................ | 52/840 |
| 6,467,357 B1 | 10/2002 | Pe | |
| 6,550,343 B2 | 4/2003 | Polega | |
| 6,598,486 B2 | 7/2003 | Vilendrer et al. | |
| 6,717,664 B2 | 4/2004 | Floyd et al. | |
| 6,976,343 B2 | 12/2005 | McGushion | |
| 6,976,396 B2 | 12/2005 | Roe et al. | |
| 7,108,290 B2 | 9/2006 | Nansen et al. | |
| 7,155,982 B2 | 1/2007 | Oesmann et al. | |

(Continued)

FOREIGN PATENT DOCUMENTS

| | | | |
|---|---|---|---|
| EP | 0328272 A2 | 8/1989 | |
| EP | 0348177 A2 | 12/1989 | |

(Continued)

OTHER PUBLICATIONS

International Search Report, dated Oct. 7, 2009, regarding Application No. PCT/US2009/048102, 5 pages.

(Continued)

*Primary Examiner* — Lisa Caputo
*Assistant Examiner* — Octavia Davis-Hollington
(74) *Attorney, Agent, or Firm* — Yee & Associates, P.C.

(57) ABSTRACT

Apparatus tests the performance of joints between an attachment and a beam having a pair of caps connected by a corrugated web. The apparatus includes first and second grips contoured to the shape of a portion of the corrugated web for gripping the web. A force applicator coupled with the attachment and the grips applies force to the beam through the joint.

11 Claims, 6 Drawing Sheets

(56) References Cited

U.S. PATENT DOCUMENTS

| | | |
|---|---|---|
| 7,392,708 B2 | 7/2008 | Bohlmann et al. |
| 7,621,187 B2 | 11/2009 | Chalmers |
| 7,665,271 B2 | 2/2010 | Kawai et al. |
| 8,286,499 B2 | 10/2012 | Foltz et al. |
| 2002/0170361 A1 | 11/2002 | Vilendrer et al. |
| 2003/0010134 A1 | 1/2003 | Polega |
| 2003/0231301 A1 | 12/2003 | Floyd et al. |
| 2005/0109119 A1 | 5/2005 | Roe et al. |
| 2006/0248959 A1 | 11/2006 | Bohlmann et al. |
| 2010/0011874 A1 | 1/2010 | Foltz et al. |

FOREIGN PATENT DOCUMENTS

| | | |
|---|---|---|
| GB | 42518 A | 12/1955 |
| WO | WO9913314 A1 | 3/1999 |
| WO | WO2006019322 A2 | 2/2006 |
| WO | WO2010011453 A1 | 1/2010 |

OTHER PUBLICATIONS

Office Action, dated Jun. 23, 2010, regarding USPTO U.S. Appl. No. 12/176,368, 12 pages.

Final Office Action, dated Dec. 7, 2010, regarding USPTO U.S. Appl. No. 12/176,368, 11 pages.

Final Office Action, dated Jun. 7, 2011, regarding USPTO U.S. Appl. No. 12/176,368, 10 pages.

Office Action, dated Jan. 6, 2012, regarding USPTO U.S. Appl. No. 12/176,368, 6 pages.

Notice of Allowance, dated Feb. 29, 2012, regarding USPTO U.S. Appl. No. 12/176,368, 9 pages.

Notice of Allowance, dated Jun. 11, 2012, regarding USPTO U.S. Appl. No. 12/176,368, 14 pages.

\* cited by examiner

METHOD AND APPARATUS FOR TESTING ATTACHMENT JOINTS

This application is a divisional of application Ser. No. 12/176,368, entitled "Method and Apparatus for Testing Attachment Joints," filed Jul. 19, 2009, status Allowed.

TECHNICAL FIELD

This disclosure generally relates to test fixtures, and deals more particularly with a test fixture apparatus and related method for testing the performance of a joint between an attachment and a beam.

BACKGROUND

It is sometimes necessary to test the performance of attachment joints. For example, in the aircraft industry, a variety of attachments such as, without limitation, stanchions, seats, partitions and other fixtures may be attached to either the top or the bottom of beams that support cargo or cabin floors. These attachments may be connected to the floor beam by various types of attachment hardware, such as, without limitation, seat tracks which are used to mount passenger seats on the floor beams. The floor beams may comprise a pair of caps connected by a web that may be either substantially straight and flat along the length of the beam, or contain non-flat and/or undulating sections. Beams having non-flat and/or undulating webs may also be known as corrugated beams, referring to the corrugated-like shape of the web.

In the past, in order to test hardware joints between an attachment and a corrugated metal floor beam, the floor beam and the attachment were connected through test fixtures to a load test machine which applied force to the floor beam that loaded the web in shear. The test fixtures, which were specially fabricated for each load test, were permanently attached to a cap and/or the corrugated metal web of the beam, thus rendering them unsuitable for reuse. The irregular shape of the corrugated web made it necessary to weld flat plates to short sections of the web in order to connect the web to the load test machine. Following a load test, the plates were not easily removed for possible reuse because they were welded to the web. Accordingly, a fresh set of plates had to be fabricated and fitted for each new load test.

Accordingly, it would be desirable to provide a method and test fixture for testing joints between attachments and beams which allow reuse of test fixture in order to reduce test cycle time, labor and materials. It would also be desirable to provide a method and test fixture that allows a moment to be applied about the attachment, as the floor beam is being shear loaded during a load test.

SUMMARY

In accordance with the disclosed embodiments, a reusable test fixture is employed to react an applied attachment load in shear through the corrugated web of a short floor beam section in order to simulate the local internal loads of a full length floor beam. The applied loads may be either axial tension loads or compression loads, with or without a moment applied to an attachment joint on the beam. The embodiments produce internal floor beam loads that closely simulate floor beam internal loads at the seat track or stanchion of an actual floor beam installed in an aircraft. Additionally, the reusable test fixture may be quickly attached to the floor beam in order to reduce test cycle time.

The test fixture is useful in rapidly generating design capability curves for multi-axis applied loads and varying corrugated floor beam geometries. The availability of these design capability curves may streamline the stress analysis process and may reduce the design/build cycle times for corrugated beams.

According to one embodiment, apparatus is provided for testing the performance of a joint between a floor beam and an attachment to the floor beam, wherein the floor beam includes a pair of caps connected by a corrugated web. The apparatus comprises first and second grips for gripping the ends of the web, and, means coupled with the attachment and the grips for applying a force through the beam. Each of the grips includes first and second portions having faces contoured to generally match the contour of the corrugated web, and at least one fastener for releasably clamping the web between the first and second grip portions.

According to another disclosed embodiment, apparatus is provided for testing the performance of a joint between a seat track and a floor beam having a corrugated web, using a short section of the floor beam as a test specimen. The apparatus comprises means for holding the opposite ends of the web of the test specimen; a load applicator for applying a load on the test specimen through the centroid of the seat track; and, a connection between the load applicator and the seat track for maintaining the direction of the applied load through the centroid of the seat track as the seat track deflects in response to the applied load.

In accordance with a further embodiment, a reusable fixture is provided for testing a short test section of a floor beam in order to simulate local internal loads on a full length beam, wherein the floor beam includes a corrugated web connected between first and second caps. The fixture comprises a load applicator for applying a load to the floor beam in a direction that loads the corrugated web in shear; a set of first reusable connections for releasably connecting the load applicator to opposite ends of the corrugated web; an attachment mounted on one of the caps; and, a second reusable connection releasably connecting the load applicator with the attachment and reacting the applied load through the attachment.

According to a disclosed method embodiment, testing the performance of a joint between an attachment and a floor beam having a pair of caps connected by a corrugated web, comprises: clamping each end of the corrugated web; and, applying a shear load to the corrugated web through the attachment. The method may further include applying a moment about the joint as the shear load is being applied to the web.

The disclosed embodiments satisfy the need for a method and apparatus for testing joints between attachments and beams having corrugated webs which overcome disadvantages of the prior test fixtures.

Other features, benefits and advantages of the disclosed embodiments will become apparent from the following description of embodiments, when viewed in accordance with the attached drawings and appended claims

BRIEF DESCRIPTION OF THE ILLUSTRATIONS

DETAILED DESCRIPTION

Figure 1:
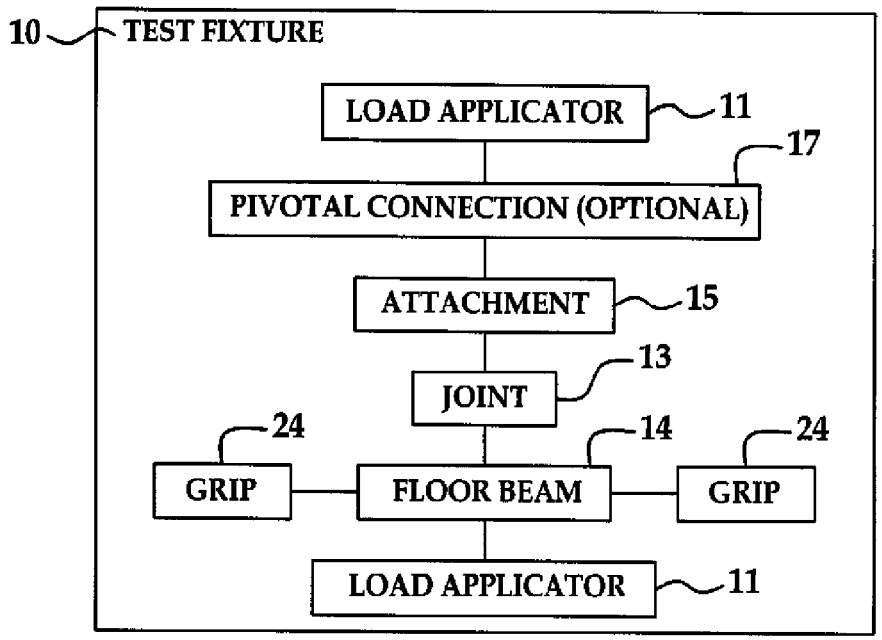
FIG. 1 is a functional block diagram of apparatus for testing joints between an attachment and a beam.

Referring first to FIG. 1, a reusable test fixture 10 includes a load applicator 11 for applying shear loads and/or bending moments through a joint 13 between an attachment 15 to a floor beam 14. The floor beam 14 is held by a pair of grips 24, and the load may be applied through a pivotal connection 17 between the load applicator and the attachment 15. As will be discussed in more detail below, the attachment 15 may comprise any of a variety of structural members, fixtures or hardware, and the floor beam 14 may comprise only a short section of a full length floor beam that is used as a test specimen to determine the performance of the joint 13 between the floor beam 14 and the attachment 15.

Figure 2:
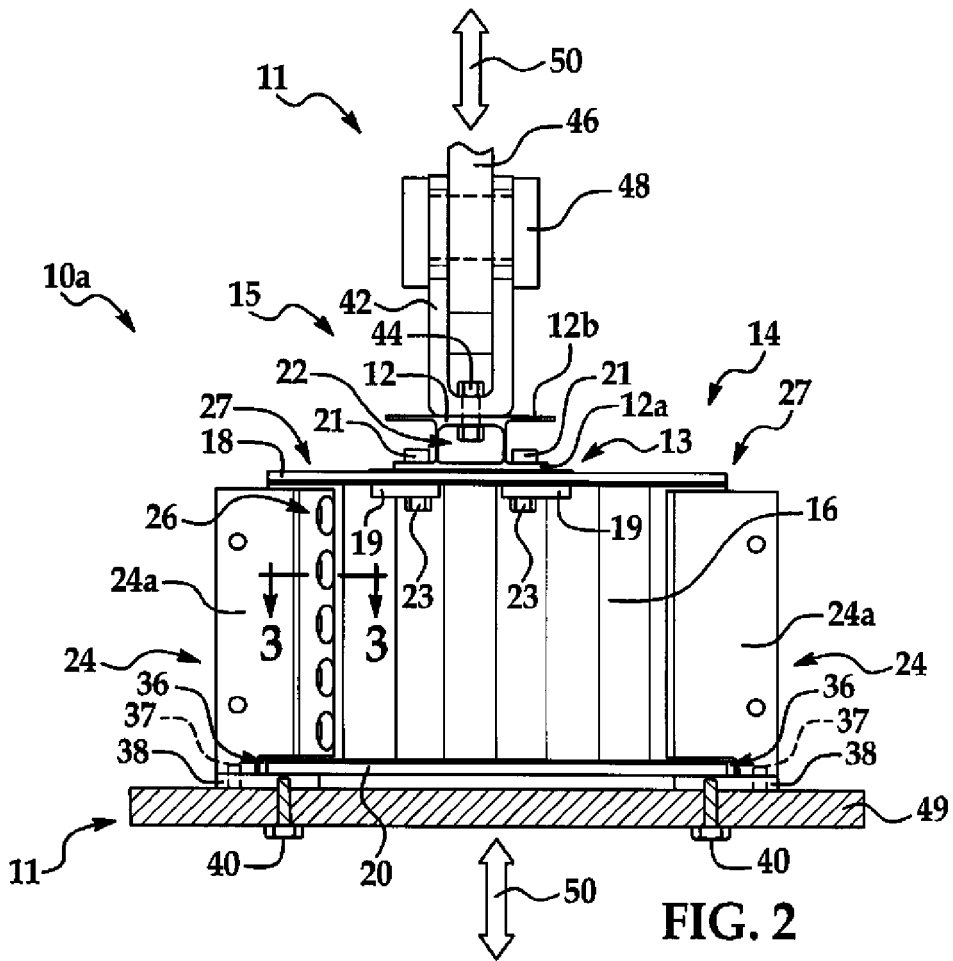
FIG. 2 is a side view of one embodiment of the apparatus.
Figure 3:
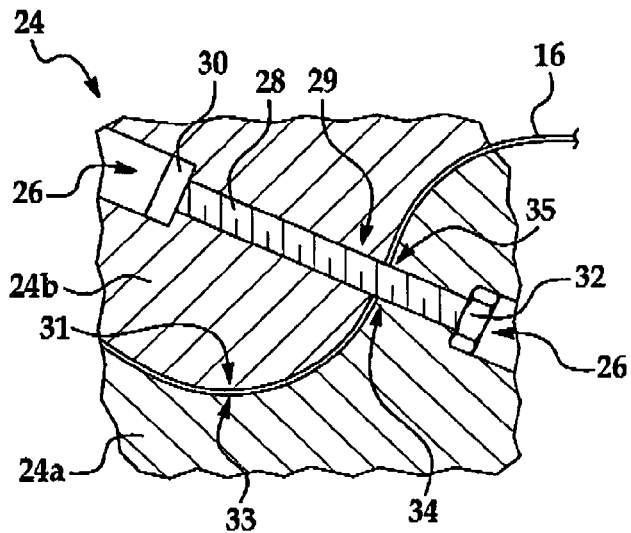
FIG. 3 is a sectional view taken along the line 3-3 in FIG. 2.

Referring now to FIGS. 2 and 3, in one embodiment, a test fixture 10a broadly includes a load applicator 11 and a pair of grips 24a for testing a joint 13 between an attachment 15 in the form of a seat track 12 and a floor beam 14. Although a seat track 12 is illustrated in FIG. 2, it is to be understood that any of various other forms of attachments, hardware, fixtures or structural members may comprise an attachment 15 to the floor beam 14. The seat track 12 includes generally flat, spaced apart flanges 12a, 12b, and a central, longitudinally extending opening 22 having a generally rectangular cross section.

The floor beam 14 comprises a pair of caps 18, 20 connected by a corrugated web 16 whose length extends from right to left as viewed in FIG. 2. The corrugated web 16 may possess any of various geometric configurations, such as, for example and without limitation, a sine wave, a square wave or a saw tooth wave. The floor beam 14 may be formed of metal, composite materials or combination of metal and composite materials. For example, the caps 18, 20 may be formed of a carbon fiber reinforced polymer resin and the web 16 may be formed of a metal such as, without limitation, titanium. The caps and the web 16 may be formed of other composite materials such as, without limitation, metallic or ceramic composites. In accordance with the disclosed embodiments, the floor beam 14 comprises a section representing a test specimen of a longer floor beam (not Shown) that may be installed in an aircraft (not shown).

The seat track 12 is fastened to the upper cap 18 by means of fasteners 21 that pass through the lower flange 12a, the upper cap 18 and radius fillers 19 that are formed on the bottom of the cap 18. Nuts 23 and washers (not shown) may be used to secure the ends of the fasteners 21 on the cap 18. The grips 24 include first and second portions 24a, 24b, each of which includes a contoured surface 31, 33 matching that of the web 16. The outer ends of the web 16 are clamped between the first and second portions 24a, 24b of the grips 24 by means of a fastener 28 that passes through a hole 35 formed in the web 16 and an opening 29 in the grip 24 which is aligned substantially normal to a generally flat section 34 of the web 16. The first and second portions 24a, 24b of the grips 24 may include countersunk holes 26 for respectively receiving the ends 30, 32 of the fastener 28. Clamping of the grips 24 to the extremities 27 of the web 16 is used to transfer the loads between the load applicator 11 and the test specimen.

The lower end of each of the grips 24 includes a recess 36 partially formed by retainer plates 38 that may be removably held on the bottom of the grips 24 by fasteners 37. The outer ends of the lower cap 20 are captured within the recess 36.

The load applicator 11 may take various forms, depending upon the particular application and load testing machine (not shown) that is used to generate the load forces. In the illustrated example, the load applicator 11 includes a U-shaped clevis 42 that is connected by a pivot pin 48 through a force applying member 46 that may apply an axial force in either direction indicated by the arrow 50. The clevis 42 may be is secured to the seat track 12 by means of a fastener 44. The pivotal connection formed between the clevis 42 and the pivot pin 48 allows a slight relative rotational moment between the force applying member 46 and the seat track 15, about the axis of pivot pin 48, thereby maintaining application of the load in the direction 50. The load applicator 11 may further include a member such as a flat plate 49 that is secured to the bottom of the grips 24 by means of the retainer plates 38 and fasteners 40. Member 49 may be stationarily mounted on a base (not shown) and thus acts as a stationary member against which the applied forces may react, or may form part of the load test machine (not shown) that applies axial force in either direction 50.

In use, a test specimen may be provided by cutting a short section of a floor beam 14 from a longer full length floor beam (not shown). The seat track 12 may then be secured to the upper cap 18 by means of suitable fasteners 21. Next, the grips 24 may be installed by positioning the first and second portions 24a, 24b on opposite sides of the web 16, near the outer extremities 27 of the floor beam 14. A hole 35 is formed in the web 16 that is aligned with the through hole opening 29 in each of the grips 24. Fasteners 28 may then be installed and tightened, thereby clamping the first and second portions 24a, 24b of the grips 24 on the ends of the web 16. The retainers 38 may be fastened to the bottom of the grips 24, thereby clamping the lower cap 20 on the grips 24. The clevis 42 is fastened to the seat track 12 using the fastener 44. The load applying member 49 may be fastened to the retainers 38 or other portions of the grips 24 using fasteners 40.

With the assembled seat track 12 and beam 14 installed in the test fixture 10a as described above, a shear load may be imposed on the web 16 through the seat track 12 by axially displacing the load applicator 11 to produce either tension or compression, as desired, in the test specimen. The load test may be either a static test that tests static properties of the test specimen, or it may be a dynamic test in which a series of either the same or different loads are applied to the test specimen. The load test may reveal information concerning the static or dynamic performance of the attachment joint 13, the attachment 15 itself, the floor beam 14, or the combination of these structural elements. Following completion of one or more the load tests, the test fixture 10a may be disassembled by simply removing the grips 24 and releasing fasteners 37, 40 and 44 which allow removal of the test specimen, thus readying the test fixture 10a for reuse with another test specimen.

Figure 4:
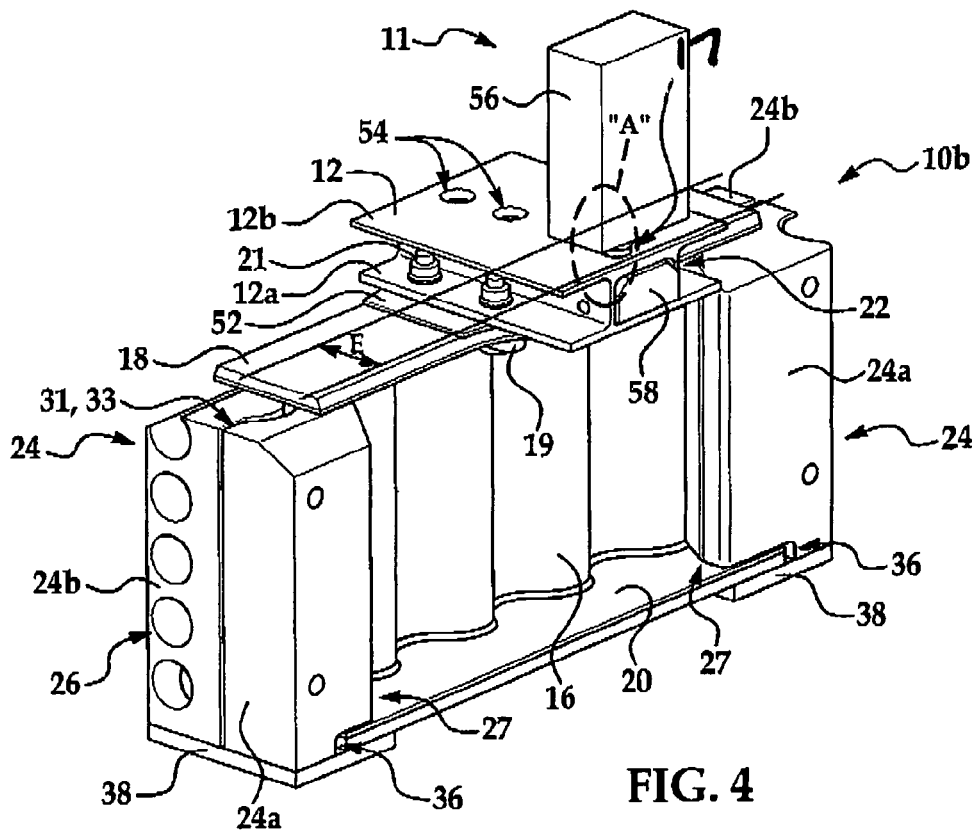
FIG. 4 is a perspective view of an alternate embodiment of the apparatus.
Figure 5:
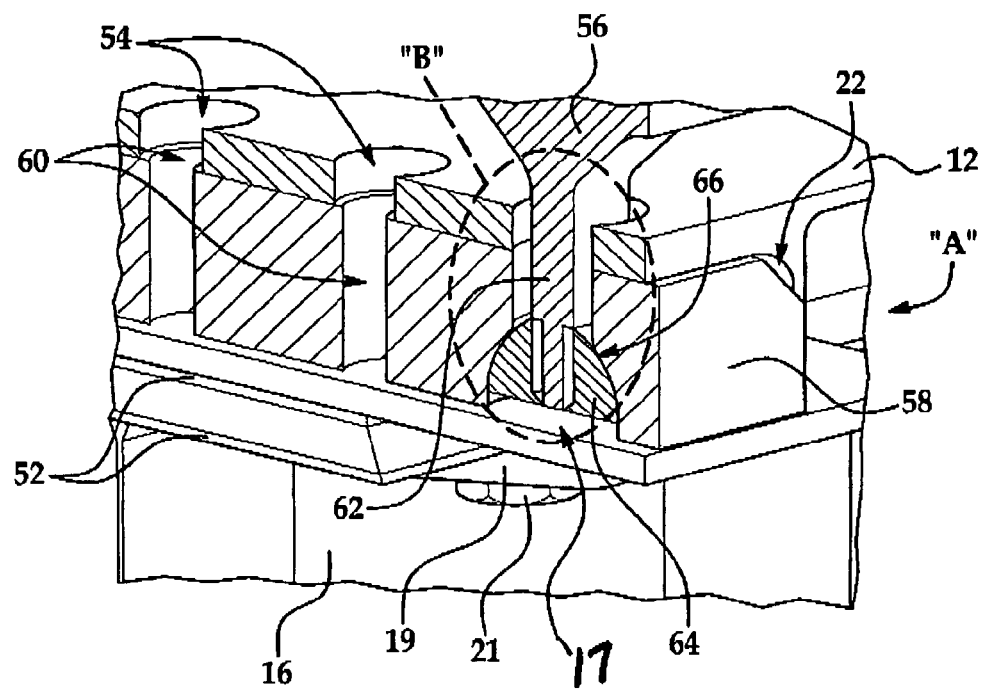
FIG. 5 is an enlarged, sectional view taken in the area designated as "A" in FIG. 4.
Figure 6:
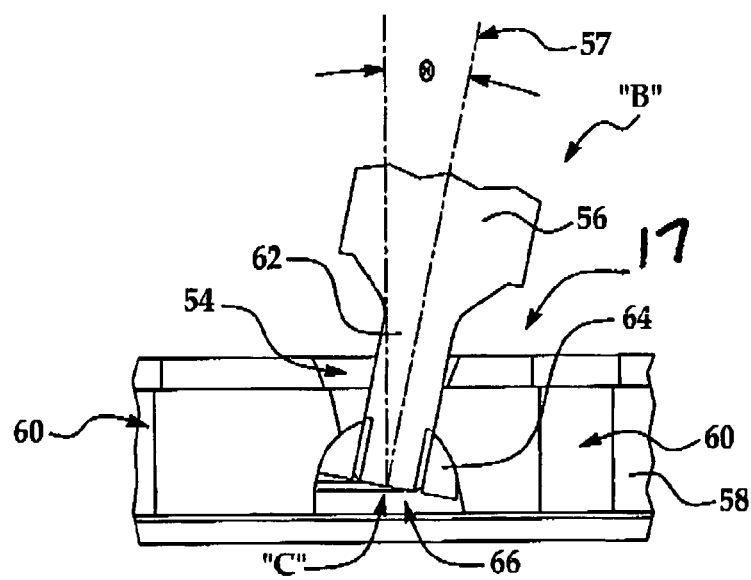
FIG. 6 is an enlarged sectional view of the area designated as "B" in FIG. 5.

Attention is now directed to FIGS. 4-6 which depict an alternate embodiment of the test fixture 10b. Test fixture 10b is similar to the test fixture 10a previously described, but further includes a semi-spherical, pivotal connection 13 between a load applicator fitting 56 and the seat track 12. The seat track 12 includes a plurality of longitudinally spaced, aligned through holes 54 in the top flange 12b that represent alternate choices for fastening a seat (not shown) to the seat track 12. When the load applicator fitting 56 is connected to the seat track 12 using one of the through holes 54 that is offset or eccentric by a distance "E" relative to the web 16, a force applied to the seat track 21 by the load applicator 11 through the fitting 56 results in both a shear load being applied to the web 16, as well as a bending moment applied being to both the seat track 12 and the flange 18, which in turn transfer the moment to the upper cap 18.

As best seen in FIGS. 5 and 6, a solid insert 58 is disposed within the longitudinal opening 22 in the seat track 12. The semi-spherical pivotal connection 13 comprises a semi-spherical lobe 64 on the end of a lug 62 forming an extension of the load applicator fitting 56. The lug 62 passes through a through hole 54 and a cylindrical passageway 60 formed in the insert 58. The insert 58 includes a semi-spherical cavity 66 that conformally engages the lobe 64, allowing the central axis 57 of the load applicator 56 to pivot and/or rotate in any direction by an angle θ until the lug 62 bottoms out on the insert 58. The size and position of the cavity 66 is chosen such that the bottom of the lobe 64 is positioned at the centroid "C" of the seat track 12. The bottom of the lug 64 remains centered at the centroid "C" regardless of the rotational/pivotal position of the load applicator fitting 56.

Figure 7:
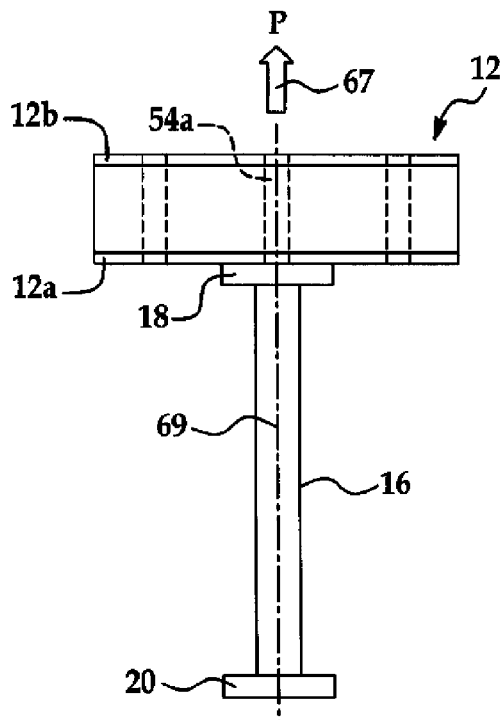
FIGS. 7 and 8 are side views illustrating the application of a moment to the floor beam shown in FIG. 4.
Figure 8:
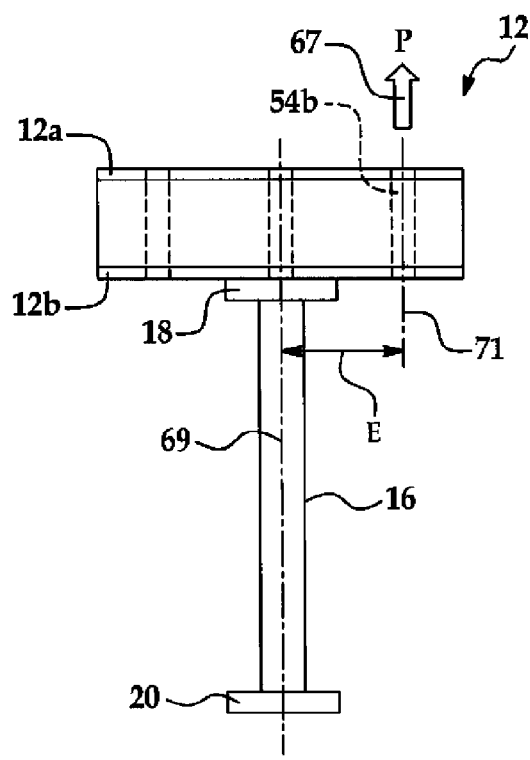

Referring now to FIG. 7, when the load applicator fitting 56 shown in FIGS. 4-6 is connected to the seat track 12 at a through hole 54a that is axially aligned with the web 16, a pulling force "P" may act in the direction of the arrow 67 along an axis 69 passing vertically through the web 16. However, as shown in FIG. 8, when the load applicator fitting 56, including the pivotal connection 17, is fastened to the seat track 12 at a through hole 54b offset from the axis 69 of web 16, the pulling force P acts along an axis 71 spaced from the web 69 by a distance "E", thereby resulting in a bending moment being applied along the length of the seat track 12 that is substantially equal to P×E. As a result of the bending moment applied to the seat track 12, both the seat track 12 and the upper cap 18 may deflect. During this deflection, the load applicator fitting 56 is allowed to rotate/pivot relative to the seat track 12 so that the axis 57 (see FIG. 6) of the force applied through the load applicator fitting 56 remains aligned with, and passes through the centroid C.

Figure 9:
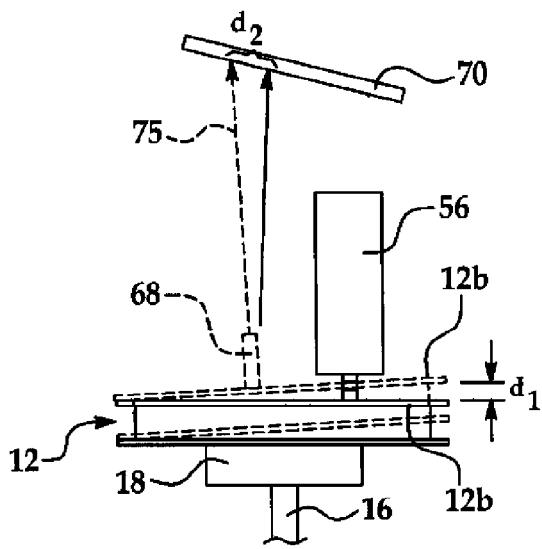
FIG. 9 is a diagram illustrating a technique for measuring the deflection of a seat track during a load test.

FIG. 9 illustrates a technique for measuring the amount of deflection produced by the bending moment applied to the seat track 12. A laser 68 or similar beam generating device, may be mounted either on the upper flange 12b of the seat track 12, or on the upper cap 18 of the beam 14. The laser 68 directs a beam 75 onto a surface 70. In response to the bending moment applied by the load applicator fitting 56, the seat track flange 12b (as well as the upper cap 18) may deflect by a distance $d_1$, causing the laser 68 to be displaced. This displacement of the laser 68 causes the laser beam 75 to be deflected by a distance $d_2$ on surface 70, proportional to, but greater than the deflection to $d_1$.

Figure 10:
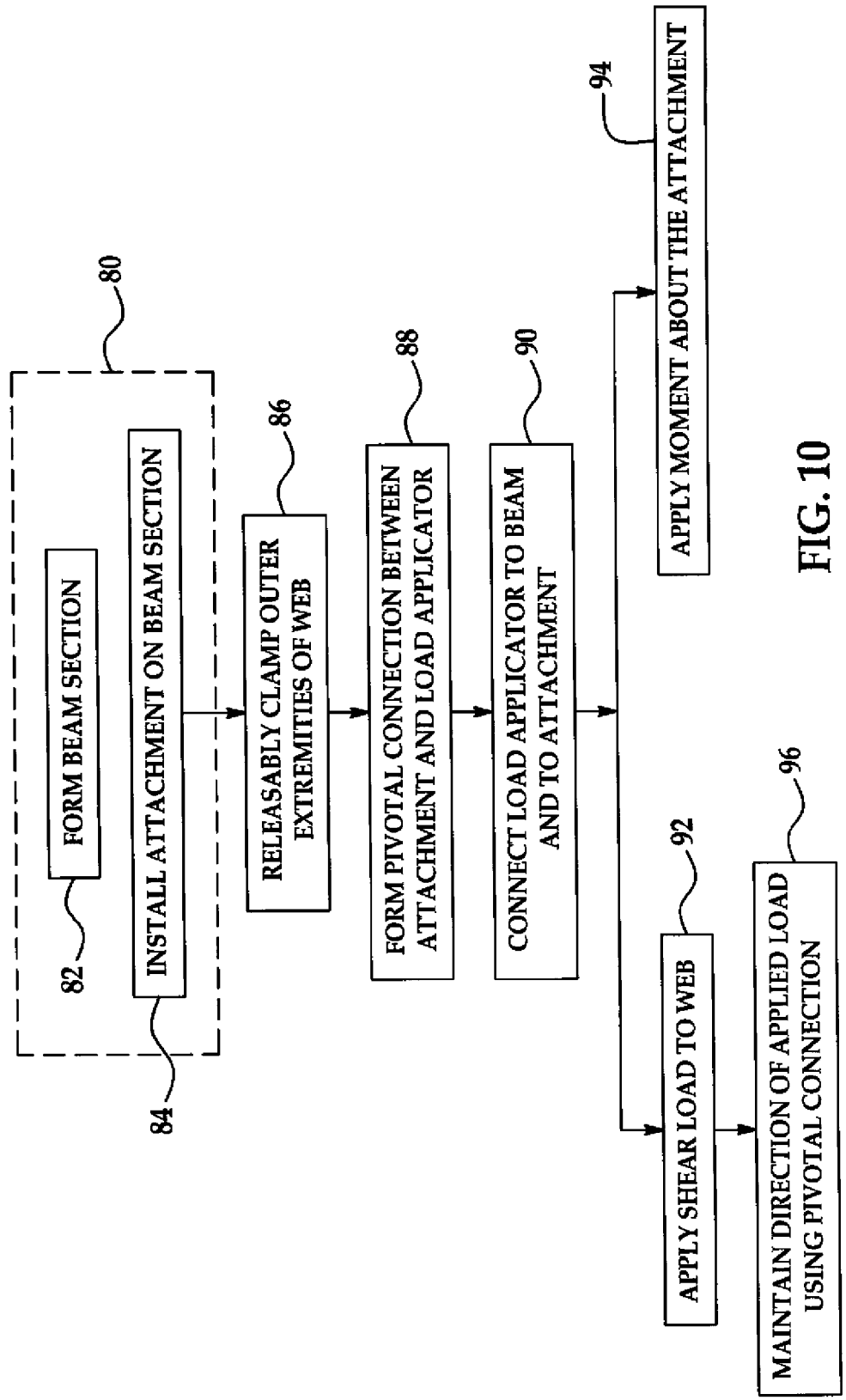
FIG. 10 is a flow diagram of a method of testing the performance of a joint between an attachment and a floor beam.

Attention is now directed to FIG. 10 which illustrates the steps of a method of testing the strength of the joint 13 between the attachment 15 and the floor beam 14 (FIG. 1). A test specimen is prepared at 80 by forming a section of floor beam 14 as shown at 82, and installing the attachment 15 on the floor beam 14, as indicated at step 84. Next, at 86, the web 16 is clamped by installing the grips 24 on the outer extremities 27 of the web 16. An optional pivotal connection 17 may be formed between the attachment 15 and the load applicator 11, as shown at step 88. At step 90, the load applicator 11 may be connected to the floor beam 14 and to the attachment 15.

Then, at step 92, a shear load may be applied to the web 16 through, without limitation, the centroid of the attachment 15. Simultaneously with step 92, a moment may be applied about the attachment 15, as shown at optional step 94. The pivotal connection 17 is used to maintain the direction of the applied load, as indicated at 96.

Figure 11:
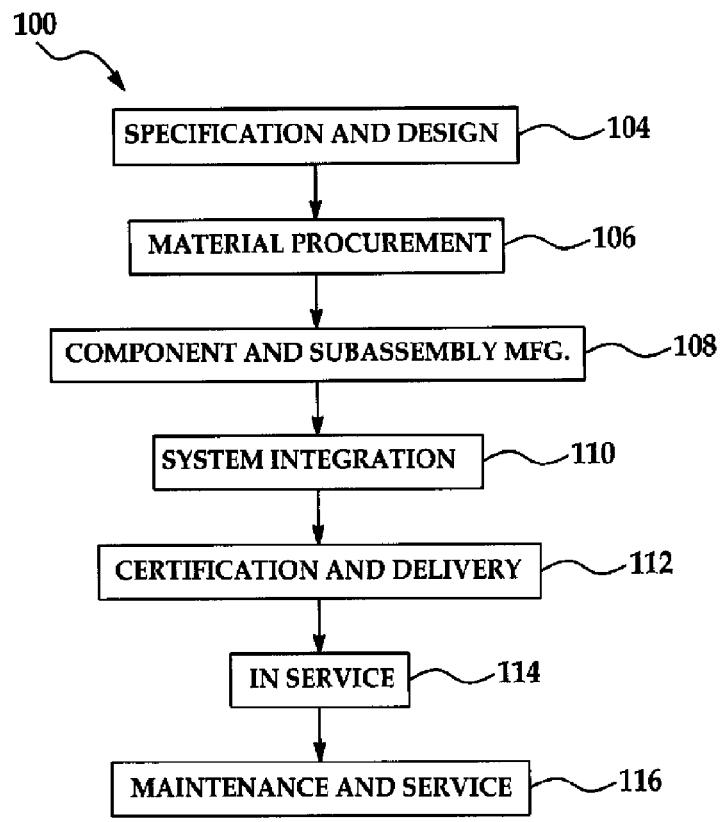
FIG. 11 is a flow diagram of aircraft production and service methodology.
Figure 12:
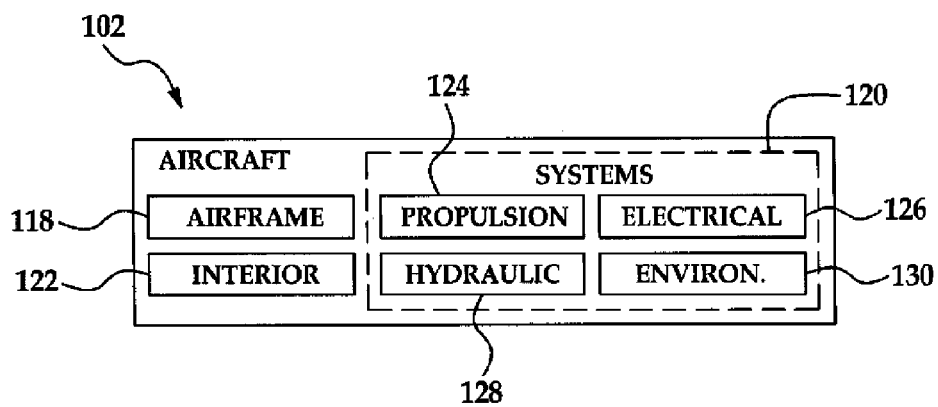
FIG. 12 is a block diagram of an aircraft.

Embodiments of the disclosure may find use in a variety of potential applications, particularly in the transportation industry, including for example, aerospace, marine and automotive applications. Thus, referring now to FIGS. 11 and 12, embodiments of the disclosure may be used in the context of an aircraft manufacturing and service method 100 as shown in FIG. 11 and an aircraft 102 as shown in FIG. 12. During pre-production, exemplary method 100 may include specification and design 104 of the aircraft 102 and material procurement 106. During production, component and subassembly manufacturing 108 and system integration 110 of the aircraft 102 takes place. Thereafter, the aircraft 102 may go through certification and delivery 112 in order to be placed in service 114. While in service by a customer, the aircraft 102 is scheduled for routine maintenance and service 96 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 12, the aircraft 102 produced by exemplary method 100 may include an airframe 118 with a plurality of systems 120 and an interior 122. Examples of high-level systems 120 include one or more of a propulsion system 124, an electrical system 126, a hydraulic system 128, and an environmental system 130. Any number of other systems may be included. Although an aerospace example is shown, the principles of the disclosure may be applied to other industries, such as the marine and automotive industries.

Systems and methods embodied herein may be employed during any one or more of the stages of the production and service method 100. For example, components or subassemblies corresponding to production process 108 may be fabricated or manufactured in a manner similar to components or subassemblies produced while the aircraft 102 is in service. Also, one or more apparatus embodiments, method embodiments, or a combination thereof may be utilized during the production stages 108 and 110, for example, by substantially expediting assembly of or reducing the cost of an aircraft 102. Similarly, one or more of apparatus embodiments, method embodiments, or a combination thereof may be utilized while the aircraft 82 is in service, for example and without limitation, to maintenance and service 116.

Although the embodiments of this disclosure have been described with respect to certain exemplary embodiments, it is to be understood that the specific embodiments are for purposes of illustration and not limitation, as other variations will occur to those of skill in the art.

What is claimed is:

1. An Apparatus for testing the performance of a joint between a seat track and a beam having a corrugated web, using a short section of the beam as a test specimen, comprising:

means for holding opposite ends of the corrugated web of the test specimen;

a load applicator for applying a load to the test specimen through a centroid of the seat track; and a connection between the load applicator and the seat track for maintaining a direction of the applied load through the centroid of the seat track as the seat track deflects in response to the applied load.

2. The apparatus of claim 1, wherein the connection includes:

an insert adapted to be inserted into the seat track and including a cavity having a semi-spherical surface, and a generally semi-spherically shaped lobe rotatable within the cavity and complementally engaging the semispherical surface of the cavity.

3. The apparatus of claim 2, wherein the connection includes:

a lug extending into the seat track and connecting the lobe with the load applicator.

4. The apparatus of claim 1, wherein the connection is laterally spaced from the corrugated web, resulting in a moment being applied to the joint by the load applicator.

5. The apparatus of claim 1, wherein the means for holding opposite ends of the corrugated web includes:

first and second grips respectively on the opposite ends of the corrugated web, and means for removably mounting the first and second grips of the web.

6. The apparatus of claim 5, wherein each of the first and second grips includes at least one face engaging, and having a contour generally matching the contour of, the corrugated web.

7. A reusable fixture for testing a short test section of a beam in order to simulate local internal loads on a full length beam, wherein the beam includes a corrugated web connected between first and second caps, comprising:

a load applicator for applying a load to the beam in a direction that loads the corrugated web in shear;

a set of first reusable connections for releasably connecting the load applicator to opposite ends of the corrugated web;

an attachment mounted on one of the caps; and a second reusable connection releasably connecting the load applicator with the attachment and reacting to the applied load through the attachment.

8. The reusable fixture of claim 7, wherein:

the set of first reusable connections includes first and second grips, each of the first and second grips including first and second portions and fasteners for clamping an end of the corrugated web between the first and second portions of the grip.

9. The reusable fixture of claim 7, wherein the second reusable connection includes a semi-spherical connection between the load applicator and the attachment and allowing the attachment to rotate relative to the load applicator.

10. A method of testing the strength of a joint between an attachment such as a seat track or a stanchion and a beam having a pair of caps connected by a corrugated web, comprising:

providing a short section of the beam;

fixing the attachment to one of the caps of the short beam section;

releasably clamping ends of the corrugated web of the short beam section;

forming a semi-spherical connection between a load applicator and the attachment;

using the load applicator to apply a shear load to the corrugated web through the attachment while applying a moment about the attachment; and, allowing the attachment to rotate relative to the load applicator through the semi-spherical connection while the moment is being applied about the attachment.

11. An Apparatus for testing the strength of a joint between an attachment such as a seat track or a stanchion and a beam having a pair of caps connected by a corrugated web, comprising:

a pair of releasable grips for gripping opposite ends of a short test section of the beam, each of the grips including first and second portions between which the web may be clamped, each of the first and second portions including opposing faces contoured to generally match the contour of the corrugated web, each of the grips further including a recess for receiving the ends of one of the caps;

retainers for retaining the ends of the one cap within the recess in each of the grips;

a load applicator for applying a shear load to the corrugated web through the attachment; and a generally semi-spherical connection between the load applicator and the attachment for maintaining the direction of the applied load through a centroid of the attachment as the attachment deflects in response the applied load.

* * * * *